(12) United States Patent
Tsuhara et al.

(10) Patent No.: US 10,577,480 B2
(45) Date of Patent: Mar. 3, 2020

(54) IMINODIACETATE CHELATING RESIN AND MANUFACTURING METHOD THEREFOR

(71) Applicant: Mitsubishi Chemical Corporation, Chiyoda-ku (JP)

(72) Inventors: Ryosuke Tsuhara, Fukuoka (JP); Masahiko Hashiguchi, Fukuoka (JP); Hirohisa Kubota, Fukuoka (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 71 days.

(21) Appl. No.: 15/839,111

(22) Filed: Dec. 12, 2017

(65) Prior Publication Data

US 2018/0100055 A1 Apr. 12, 2018

Related U.S. Application Data

(63) Continuation of application No. PCT/JP2016/068426, filed on Jun. 21, 2016.

(30) Foreign Application Priority Data

Jun. 22, 2015 (JP) .................................. 2015-124787

(51) Int. Cl.
*C08F 8/30* (2006.01)
*C08K 5/17* (2006.01)
(Continued)

(52) U.S. Cl.
CPC ............ *C08K 5/175* (2013.01); *C07C 229/24* (2013.01); *C08F 8/12* (2013.01); *C08F 8/24* (2013.01);
(Continued)

(58) Field of Classification Search
CPC ...... C08F 8/32; C08F 8/12; C08F 8/26; C08F 212/36; C08F 212/14
See application file for complete search history.

(56) References Cited

U.S. PATENT DOCUMENTS 3,899,472 A * 8/1975 Aya ........................... C08F 8/32
521/32
4,358,546 A * 11/1982 Naomi ..................... C08F 8/30
521/32

(Continued)

FOREIGN PATENT DOCUMENTS

GB 767821 2/1957
JP 50-80387 6/1975
(Continued)

OTHER PUBLICATIONS

Translation of JP S59-70656 (19840 (Year: 1984).*
(Continued)

*Primary Examiner* — Robert C Boyle
(74) *Attorney, Agent, or Firm* — Oblon, McClelland, Maier & Neustadt, L.L.P.

(57) ABSTRACT

The present invention relates to an iminodiacetic acid chelating resin, wherein the water amount in the resin is from 50 to 75% and the volume ratio of Na form/H form is from 1.4 to 1.8. Furthermore, the present invention relates to a method for producing an iminodiacetic acid chelating resin, wherein an alcohol is used as a solvent for the amination reaction of a chloromethylated styrene crosslinked copolymer with iminodiacetonitrile or sodium iodide and/or potassium iodide is used as a catalyst for the amination reaction.

13 Claims, 1 Drawing Sheet

(51) Int. Cl.
*C08F 8/24* (2006.01)
*C08F 8/12* (2006.01)
*C07C 229/24* (2006.01)
*C08F 12/18* (2006.01)
*C08F 12/28* (2006.01)
*C08F 14/14* (2006.01)
*C08G 69/26* (2006.01)
*C08J 7/12* (2006.01)
*C08J 7/14* (2006.01)

(52) U.S. Cl.
CPC ............... *C08F 8/30* (2013.01); *C08F 12/18* (2013.01); *C08F 12/28* (2013.01); *C08F 14/14* (2013.01); *C08G 69/26* (2013.01); *C08J 7/126* (2013.01); *C08J 7/14* (2013.01)

(56) References Cited

U.S. PATENT DOCUMENTS

| | | | |
|---|---|---|---|
| 5,804,606 | A | 9/1998 | Surowiec et al. |
| 6,410,656 | B1 | 6/2002 | Kubota et al. |
| 2002/0193454 | A1 | 12/2002 | Lutjens et al. |
| 2011/0132844 | A1 | 6/2011 | Klipper et al. |

FOREIGN PATENT DOCUMENTS

| | | |
|---|---|---|
| JP | 52-22092 | 2/1977 |
| JP | 53-121897 | 10/1978 |
| JP | 56-161404 | 12/1981 |
| JP | 59-71308 | 4/1984 |
| JP | S59-70656 | * 4/1984 |
| JP | 62-125860 | 6/1987 |
| JP | 5-320233 | 12/1993 |
| JP | 10-296095 | 11/1998 |
| JP | 2000-61320 | 2/2000 |
| JP | 2011-137136 | 7/2011 |
| JP | 2016-8219 | 1/2016 |
| WO | WO 98/04598 | 2/1998 |

OTHER PUBLICATIONS

International Search Report dated Aug. 16, 2016 in PCT/JP2016/068426, filed on Jun. 21, 2016 (with English Translation).
Written Opinion dated Aug. 16, 2016 in PCT/JP2016/068426, filed on Jun. 21, 2016.
Kobunshi Kagaku (Polymer Chemistry),vol. 17, No. 177, 1960, pp. 4.
Mitsuo Yamada et al. "Synthesis and Chelating Behavior of Bis(Carboxymethyl) Iminomethylene Derivative of Oligomeric Styrene," J.Coord.Chem., 1980, vol. 10, pp. 6.
Combined Chinese Office Action and Search Report dated May 8, 2019 in Patent Application No. 201680036264.X, 16 pages (with English translation and English Translation of Category of Cited Documents).

* cited by examiner

IMINODIACETATE CHELATING RESIN AND MANUFACTURING METHOD THEREFOR

TECHNICAL FIELD

The present invention relates to an iminodiacetic acid chelating resin, and a production method thereof. More specifically, the present invention relates to an iminodiacetic acid chelating resin with excellent separation capacity. In addition, the present invention relates to a method for producing an iminodiacetic acid chelating resin, where an iminodiacetic acid group can be effectively introduced into a chloromethylated styrene crosslinked copolymer under mild conditions.

BACKGROUND ART

An iminodiacetic acid chelating resin has high capability of selectively adsorbing a heavy metal and is widely used in the fields such as heavy metal removal from salt and purification of chemicals.

As the production method of an iminodiacetic acid chelating resin, there have been conventionally known, for example, a method of synthesizing an aminomethylated polymer by the phthalimide process and reacting the polymer with chloroacetic acid (Patent Document 1), a method of reacting hexamethylenetetramine with a chloromethylated polymer to synthesize an aminomethylated polymer and reacting the polymer with chloroacetic acid (Patent Document 2), a method of reacting a chloromethylated styrene crosslinked copolymer with iminodiacetonitrile (Non-Patent Document 1), a method of reacting a chloromethylated styrene crosslinked copolymer with an iminodiacetic acid ester (Non-Patent Document 2), and a method using a chloromethylated styrene crosslinked copolymer as a raw material, wherein hydrophilicity is imparted to the matrix of the crosslinked copolymer by use of dimethylaniline as a catalyst and the copolymer is reacted with iminodiacetonitrile (Patent Document 3).

In this connection, in Non-Patent Document 1, a chloromethylated styrene crosslinked copolymer is reacted with iminodiacetonitrile by using pyridine as a solvent and then hydrolyzed.

BACKGROUND ART LITERATURE

Patent Document

Patent Document 1: JP-A-2000-61320
Patent Document 2: JP-A-10-296095
Patent Document 3: UK Patent No. 767821

Non-Patent Document

Non-Patent Document 1: *Kobunshi Kagaku (Polymer Chemistry)*, 1960, Vol. 17, No. 177, 30-36
Non-Patent Document 2: *J. Coord. Chem.*, 1980, Vol. 10, 257-262

SUMMARY OF THE INVENTION

Problems to be Solved by the Invention

In using an iminodiacetic acid chelating resin in various fields, although it is required to more improve the separation capacity, i.e., metal adsorption capacity, this requirement has not yet been achieved by an iminodiacetic acid chelating resin produced by the above-described conventional methods.

The present invention has been made taking into account the problems of those conventional techniques and aims at providing an iminodiacetic acid chelating resin having excellent separation capacity. The present invention also aims at providing a method for producing an iminodiacetic acid chelating resin, where an iminodiacetic acid group can be effectively introduced into a chloromethylated styrene crosslinked copolymer under mild conditions.

Means for Solving the Problems

As a result of intensive studies, the present inventors have found that in the iminodiacetic acid chelating resin, when the amount introduced, etc. of an iminodiacetic acid group is controlled, the adsorption amount of a metal such as Cu can be enhanced. It has been also found that in the method for producing an iminodiacetic acid chelating resin by aminating a chloromethylated styrene crosslinked copolymer with iminodiacetonitrile and then hydrolyzing the copolymer, when a specific solvent or a specific catalyst is used for the amination reaction, an iminodiacetic acid group can be efficiently introduced into the chloromethylated styrene crosslinked copolymer under mild conditions. The present invention has been accomplished based on these findings.

Namely, the gist of the present invention is as follows.

[1] An iminodiacetic acid chelating resin wherein the infrared absorption spectrum obtained by infrared absorption analysis satisfies the following formula (1):

$$0.85\% \leq (\text{transmittance at 2,000 cm}^{-1})-(\text{transmittance at 2,200 cm}^{-1}))/(\text{transmittance at 2,000 cm}^{-1}) \times 100 \leq 5\% \quad (1)$$

[2] The iminodiacetic acid chelating resin according to [1], wherein the water amount in the resin is from 50 to 75%.

[3] The iminodiacetic acid chelating resin according to [1] or [2], wherein the volume ratio of Na form/H form is from 1.2 to 1.8.

[4] An iminodiacetic acid chelating resin, wherein the water amount in the resin is from 50 to 75% and the volume ratio of Na form/H form is from 1.4 to 1.8.

[5] The iminodiacetic acid chelating resin according to any one of [1] to [4], wherein the infrared absorption spectrum obtained by infrared absorption analysis has a downwardly convex peak in the range of 2,100 to 2,300 $cm^{-1}$.

[6] The iminodiacetic acid chelating resin according to any one of [1] to [5], wherein the degree of porosity is from 60 to 90%.

[7] The iminodiacetic acid chelating resin according to any one of [1] to [6], wherein the degree of crosslinking is from 4 to 7%.

[8] A method for producing an iminodiacetic acid chelating resin, containing aminating a chloromethylated styrene crosslinked copolymer with iminodiacetonitrile, and hydrolyzing the aminated styrene crosslinked copolymer, wherein:
an alcohol is used as a solvent for the amination reaction.

[9] The method for producing an iminodiacetic acid chelating resin according to [8], wherein sodium iodide and/or potassium iodide is used as a catalyst for the amination reaction.

[10] A method for producing an iminodiacetic acid chelating resin, containing aminating a chloromethylated styrene crosslinked copolymer with iminodiacetonitrile, and hydrolyzing the aminated styrene crosslinked copolymer, wherein:

sodium iodide and/or potassium iodide is used as a catalyst for the amination reaction.

[11] The method for producing an iminodiacetic acid chelating resin according to [9] or [10], wherein the used amount of the catalyst is from 0.1 to 30 parts by weight per 100 parts by weight (on dry resin basis) of the chloromethylated styrene crosslinked copolymer.

[12] The method for producing an iminodiacetic acid chelating resin according to any one of [8] to [11], wherein the used amount of the iminodiacetonitrile is from 40 to 200 parts by weight per 100 parts by weight (on dry resin basis) of the chloromethylated styrene crosslinked copolymer.

[13] The method for producing an iminodiacetic acid chelating resin according to any one of [8] to [12], wherein in the amination reaction, the reaction temperature is from 40 to 120° C. and the reaction time is from 0.5 to 15 hours.

[14] The method for producing an iminodiacetic acid chelating resin according to any one of [8] to [13], wherein the boiling point of the solvent for the amination reaction is from 30 to 180° C. and the used amount of the solvent is from 100 to 3,000 parts by weight per 100 parts by weight (on dry resin basis) of the chloromethylated styrene crosslinked copolymer.

[15] The method for producing an iminodiacetic acid chelating resin according to any one of [8] to [14], wherein an aliphatic alcohol containing branched chain and having a carbon number of 3 to 4 is used as a solvent for the amination reaction.

[16] The method for producing an iminodiacetic acid chelating resin according to any one of [8] to [15], wherein the hydrolysis reaction is performed in the presence of at least one aqueous alkali solution selected from the group consisting of an aqueous sodium hydroxide solution, an aqueous potassium hydroxide solution and an aqueous calcium hydroxide solution, or at least one strong acid selected from the group consisting of sulfuric acid, hydrochloric acid and nitric acid.

[17] An iminodiacetic acid chelating resin wherein the iodine concentration in a supernatant after addition of water 10 of times the weight of an iminodiacetic acid chelating resin to the iminodiacetic acid chelating resin and shaking at 30° C. for 8 hours is 10 ng/g or more.

Effect of the Invention

The iminodiacetic acid chelating resin of the present invention has excellent separation capacity, i.e., metal adsorption capacity.

According to the production method of an iminodiacetic acid chelating resin of the present invention, an iminodiacetic acid group can be efficiently introduced into a chloromethylated styrene crosslinked copolymer under mild conditions. In addition, the obtained iminodiacetic acid chelating resin has excellent heavy metal adsorptivity, since the amount introduced of an iminodiacetic acid group is large.

MODE FOR CARRYING OUT THE INVENTION

Although embodiments of the present invention are described in detail below, the present invention is not limited to the following explanations and can be implemented by arbitrarily making a modification without departing from the gist of the invention. Here, in the present description, when a range is expressed by using "to" and giving numerical values or property values before and after the term, this means that the range includes the numerical values or property values.

(1) A first embodiment of the iminodiacetic acid chelating resin of the present invention is as follows:

an iminodiacetic acid chelating resin wherein the infrared absorption spectrum obtained by infrared absorption analysis satisfies the following formula (1):

$$0.85\% \leq ((\text{transmittance at } 2{,}000 \text{ cm}^{-1}) - (\text{transmittance at } 2{,}200 \text{ cm}^{-1}))/(\text{transmittance at } 2{,}000 \text{ cm}^{-1}) \times 100 \leq 5\% \quad (1)$$

(2) A second embodiment of the iminodiacetic acid chelating resin of the present invention is as follows:

an iminodiacetic acid chelating resin, wherein the water amount in the resin is from 50 to 75% and the volume ratio of Na form/H form is from 1.4 to 1.8.

(3) A first embodiment of the production method of an iminodiacetic acid chelating resin of the present invention is as follows:

a method for producing an iminodiacetic acid chelating resin, including aminating a chloromethylated styrene crosslinked copolymer with iminodiacetonitrile, and hydrolyzing the aminated styrene crosslinked copolymer, wherein an alcohol is used as a solvent for the amination reaction.

(4) A second embodiment of the production method of an iminodiacetic acid chelating resin of the present invention is as follows:

a method for producing an iminodiacetic acid chelating resin, including aminating a chloromethylated styrene crosslinked copolymer with iminodiacetonitrile, and hydrolyzing the aminated styrene crosslinked copolymer, wherein sodium iodide and/or potassium iodide is used as a catalyst for the amination reaction.

For the convenience of explanation, the production method of an iminodiacetic acid chelating resin of the present invention is firstly explained, and the iminodiacetic acid chelating resin of the present invention is then explained.

[Production Method of Iminodiacetic Acid Chelating Resin]

<Amination Reaction>

The production method of an iminodiacetic acid chelating resin of the present invention is characterized in that at the time of performing an amination reaction of a raw material, i.e., a chloromethylated styrene crosslinked copolymer, by using iminodiacetonitrile as an aminating agent to produce an aminated styrene crosslinked copolymer, the following condition (1) and/or (2) is employed:

(1) An alcohol is used as a solvent; and (2) Sodium iodide and/or potassium iodide is used as a catalyst.

A chloromethylated styrene crosslinked copolymer used in the production method of the present invention can be obtained by performing a chloromethylation reaction of a styrene crosslinked copolymer in a usual manner, for example, by the method described in JP-A-5-320233, JP-A-2010-42395, etc. The chloromethylated styrene crosslinked copolymer can also be obtained by copolymerizing a chloromethylstyrene monomer with another copolymerizable monomer such as styrene.

The "styrene crosslinked copolymer" as used in the present invention is a crosslinked polymer obtained by copolymerizing a monovinyl aromatic monomer and a crosslinking aromatic monomer and can be obtained in a usual manner, for example, by the method described in JP-A-5-320233, JP-A-2010-42395, etc. In this connection, although the styrene crosslinked copolymer may be a gel type or a porous type, as described later, the iminodiacetic acid chelating resin of the present invention preferably has a degree of porosity of 60 to 90% and therefore, in the case of producing the iminodiacetic acid chelating resin of the present invention by the production method of an iminodiacetic acid chelating resin of the present invention, the styrene crosslinked copolymer is preferably a porous type.

The monovinyl aromatic monomer as a raw material of the styrene crosslinked copolymer includes styrene, alkyl-substituted styrenes such as methyl styrene and ethylstyrene, and halogen-substituted styrenes such as bromostyrene. One of these may be used alone, or two or more thereof may be mixed and used. The monovinyl aromatic monomer is preferably styrene or a monomer based on styrene. The term "based on" as used herein means to account for 50% by weight or more, preferably from 70 to 100% by weight, of the total.

The crosslinking aromatic monomer as another raw material of the styrene crosslinked copolymer includes divinylbenzene, trivinylbenzene, divinyltoluene, divinylnaphthalene, divinylxylene, divinylbiphenyl, bis(vinylphenyl)methane, bis(vinylphenyl)ethane, bis(vinylphenyl)propane, bis(vinylphenyl)butane, etc. One of these may be used alone, or two or more thereof may be mixed and used. Among others, the crosslinking aromatic monomer is preferably divinylbenzene. In this connection, a significant amount of ethylvinylbenzene (ethylstyrene) as a byproduct is usually contained in industrially produced divinylbenzene, and such divinylbenzene can also be used in the present invention.

The degree of crosslinking of the styrene crosslinked copolymer is usually from 3 to 20%, and preferably from 5 to 15%. The term "degree of crosslinking" as used herein means a ratio (% by weight) of a crosslinking aromatic monomer to the total amount of a monovinyl aromatic monomer and a crosslinking aromatic monomer, which are used as raw materials of the styrene crosslinked copolymer.

The degree of crosslinking of the iminodiacetic acid chelating resin of the present invention is preferably from 4 to 7% as described later. Accordingly, in the case of producing the later-described iminodiacetic acid chelating resin of the present invention by the production method of an iminodiacetic acid chelating resin of the present invention, raw material monomers are preferably used to satisfy the degree of crosslinking in the range above.

In the case of producing the iminodiacetic acid chelating resin of the present invention preferably having a degree of porosity of 60 to 90% by the production method of an iminodiacetic acid chelating resin of the present invention, an organic solvent is caused to be present as a porosifying agent (precipitant) in the reaction at the time of production of the styrene crosslinked copolymer. As the organic solvent, a poor solvent for the raw material monomer is used and, for example, in the case of producing a styrene-divinylbenzene crosslinked copolymer where the main raw material monomer is styrene, one member or two or more members of benzene, toluene, xylene, heptane, dodecane, isooctane (2,2,4-trimethylpentane), 2-ethylhexanol, tert-amyl alcohol, decanol, methyl isobutyl ketone, diisobutyl ketone, etc. may be used.

The degree of porosity of the iminodiacetic acid chelating resin is a measure indicating the sparse/dense of pore structure of the iminodiacetic acid chelating resin and is defined by a ratio (% by weight) of the amount of an organic solvent as a porosifying agent relative to all raw material monomers charged at the time of production of the styrene crosslinked copolymer. Accordingly, in the case of producing the iminodiacetic acid chelating resin of the present invention by the production method of an iminodiacetic acid chelating resin of the present invention, the organic solvent is preferably used such that the ratio of the organic solvent as a porosifying agent becomes from 60 to 90% by weight, particularly from 65 to 88% by weight, more particularly from 70 to 85% by weight, still more particularly from 75 to 83% by weight, relative to all raw material monomers charged.

In the amination reaction of a chloromethylated styrene crosslinked copolymer, the amount of iminodiacetonitrile used as an aminating agent is, per 100 parts by weight of the dried chloromethylated styrene crosslinked copolymer (i.e., on dry resin basis), preferably 40 parts by weight or more, more preferably 60 parts by weight or more, still more preferably 80 parts by weight or more, and on the other hand, is preferably 200 parts by weight or less, more preferably 180 parts by weight or less, still more preferably 150 parts by weight or less.

When the used amount of iminodiacetonitrile is 40 parts by weight or more, the introduction efficiency of a functional group increases, and the metal adsorption capacity of the obtained iminodiacetic acid chelating resin is enhanced. On the other hand, when the used amount is 200 parts by weight or less, the amount of the remaining unreacted aminating agent can be reduced, and the aminating agent can be efficiently used for the reaction.

In this connection, the "dried chloromethylated styrene crosslinked copolymer" as used in the present invention means a chloromethylated styrene crosslinked copolymer that is vacuum-dried at 50° C. for 8 hours or more.

In the production method of the present invention, the solvent for the amination reaction may be sufficient if it is an inert solvent which does not participate in the reaction or does not inhibit the reaction, and an alcohol exemplified below, the later-described solvent exemplified as another solvent except for an alcohol, aromatic hydrocarbons such as toluene, ethers such as 1,4-dioxane and tetrahydrofuran, a halogen-based solvent such as 1,2-dichloroethane, and an organic solvent such as dimethylsulfoxide and dimethylformamide, may be used. Among others, for the reason that an iminodiacetic acid group can be efficiently introduced into the chloromethylated styrene crosslinked copolymer under mild conditions and at the same time, the post-treatment of the obtained iminodiacetic acid chelating resin is facilitated, an alcohol is preferably used.

As the alcohol, a linear alcohol or a branched chain alcohol may be used.

The linear alcohol includes, specifically, a linear aliphatic alcohol such as methanol, ethanol, propanol and butanol.

The branched chain alcohol includes, specifically, a branched aliphatic alcohol such as isopropanol, isobutanol, isopentyl alcohol, isohexyl alcohol, isoheptyl alcohol, isooctyl alcohol, isononyl alcohol and isodecyl alcohol.

One of these may be used alone, or two or more thereof may be mixed and used.

Although details of the operational mechanism by which in an amination reaction, use of an alcohol as a solvent enables an iminodiacetic acid group to be efficiently introduced into the chloromethylated styrene crosslinked copolymer under mild conditions are not clearly known, it is presumed that when an alcohol is used, porosity of the choromethylated styrene crosslinked copolymer proceeds, making it easy for a raw material compound such as iminodiacetonitrile as an aminating agent to enter inside the resin, and the amination reaction can thereby be efficiently performed. In addition, the introduced amount of an iminodiacetic acid group can be optimally controlled due to use of an alcohol and consequently, an iminodiacetic acid chelating resin having a high metal adsorption amount can be obtained.

The alcohol used as a solvent for the amination reaction is preferably an alcohol which is an inert solvent which does not participate in the reaction or does not inhibit the reaction and has a boiling point of 30 to 180° C. In the case of a branched chain alcohol, the alcohol is preferably an aliphatic alcohol having a carbon number of 3 to 6, such as isopropanol (boiling point: 82° C.), isobutanol (boiling point: 108° C.), isopentyl alcohol (boiling point: 131° C.) and isohexyl alcohol (boiling point: from 160 to 165° C.), more preferably an aliphatic alcohol having a carbon number of 3 or 4, still more preferably isopropanol. A solvent having a boiling point of 30 to 180° C. is preferred in that the control/handling is easy or the recovery by distillation, etc. is facilitated. In the case of a linear alcohol, the alcohol is preferably an aliphatic alcohol having a carbon number of 1 to 4, such as methanol (boiling point: 65° C.), ethanol (boiling point: 78° C.), 1-propanol (boiling point: 97° C.) and 1-butanol (boiling point: 117° C.).

The used amount of the solvent such as alcohol, per 100 parts by weight of the dried chloromethylated styrene crosslinked copolymer (i.e., on dry resin basis), is preferably 100 parts by weight of more, more preferably 200 parts by weight or more, still more preferably 300 parts by weight of more, and yet still more preferably 500 parts by weight or more, and on the other hand, is preferably 3,000 parts by weight of less, more preferably 2,000 parts by weight or less, and still more preferably 1,000 parts by weight or less.

Especially in the case of using an alcohol as a solvent, when the used amount of the alcohol is 100 parts by weight or more per 100 parts by weight of the dried chloromethylated styrene crosslinked copolymer (i.e., on dry resin basis), the above-described effects due to use of an alcohol can be effectively brought out, and on the other hand, when the used amount is 3,000 parts by weight or less, the productivity can be increased by preventing the volume of the reaction from becoming excessively large.

In the present invention, another solvent except for an alcohol may be used as a solvent for the amination reaction, or an alcohol and another solvent except for an alcohol may be used in combination. The another solvent is also preferably a solvent that is an inert solvent which does not participate in the reaction or does not inhibit the reaction and has a boiling point of 30 to 180° C., and such an inert solvent includes saturated hydrocarbons, an ether compound, an organic halide, water, etc., which have a boiling point in the range above.

As for specific examples of the another solvent except for an alcohol, which can be used in the present invention, the saturated hydrocarbons include, for example, pentane (boiling point: 36° C.), hexane, heptane, octane, nonane, and decane (boiling point: 174° C.); the ether compound includes, for example, methylal (boiling point: 42° C.), 1,4-dioxane, and tetrahydrofuran; and the organic halide includes, for example, dichloromethane, 1,2-dichloroethane (boiling point: 84° C.), and chloroform. One of these may be used alone, or two or more thereof may be mixed and used.

In the case of using an alcohol and another solvent except for an alcohol in combination, the another solvent is preferably used in a ratio of 50% by weight or less, preferably 30% by weight or less, relative to the total of the alcohol and another solvent. In the present invention, it is preferable to use only an alcohol as a solvent.

The amination reaction in the present invention may use a catalyst, and sodium iodide and/or potassium iodide is preferably used as the catalyst. It is considered that iodine atom in the sodium iodide and potassium iodide provides high-efficient substitution with a chloromethyl group of the chloromethylated crosslinked copolymer and the moiety subjected to substitution due to iodine atom is increased in the reactivity with iminodiacetonitrile as an aminating agent, as a result, the amination reaction is allowed to efficiently proceed under mild conditions.

The sodium iodide and/or potassium iodide as a catalyst is preferably used in an amount of 0.1 to 30 parts by weight per 100 parts by weight of the dried chloromethylated styrene crosslinked copolymer (i.e., on dry resin basis). The lower limit value of the used amount of sodium iodide and/or potassium iodide is more preferably 3 parts by weight or more, still more preferably 5 parts by weight or more, yet still more preferably 10 parts by weight or more, and on the other hand, the upper limit value is more preferably 25 part by weight or less, still more preferably 20 parts by weight or less, yet still more preferably 18 parts by weight or less.

The used amount of sodium iodide and/or potassium iodide is preferably not less than the lower limit value above from the viewpoint of allowing the reaction to efficiently proceed, and on the other hand, the used amount is preferably not more than the upper limit value above from the viewpoint of decreasing the catalyst residue in the obtained iminodiacetic acid chelating resin.

In the case of using sodium iodide and/or potassium iodide as a catalyst, iodine often remains as a catalyst residue in the obtained iminodiacetic acid chelating resin. For example, when water is added to the obtained iminodiacetic acid chelating resin and a supernatant after shaking is analyzed by TCP-MS, ion chromatography, etc., iodine is detected. Specifically, when the iodine concentration in a supernatant after addition of water 10 times of the weight of an iminodiacetic acid chelating resin to the resin and shaking at 30° C. for 8 hours is 10 ng/g or more, particularly 50 ng/g or more, more particularly 100 ng/g or more, and still more particularly 500 ng/g or more, it is believed that sodium iodide and/or potassium iodide is used as a catalyst for the amination reaction.

The iodine concentration in a supernatant is specifically measured by the method described later in the section of Examples.

In the amination reaction, in addition to sodium iodide and/or potassium iodide, another catalyst may be used in the range which does not significantly impair the effects of the present invention. Another catalyst includes, for example, dimethylaniline.

Furthermore, a basic substance is preferably caused to present together at the time of starting the reaction. For example, a basic substance such as sodium carbonate, sodium hydrogencarbonate and potassium carbonate may be used in an amount of approximately from 5 to 500 parts by weight per 100 parts by weight of the dried chloromethylated styrene crosslinked copolymer (i.e., on dry resin basis). The lower limit value of the used amount of the basic substance is more preferably 10 parts by weight or more, and still more preferably 20 parts by weight or more, and on the other hand, the upper limit value is more preferably 300 part by weight or less, still more preferably 200 parts by weight or less, and yet still more preferably 100 parts by weight or less. One of the above-described basic substances may be used alone, or two or more thereof may be used in combination.

In the amination reaction, the lower limit of the reaction temperature is preferably 40° C. or more, and more preferably 60° C. or more, and the upper limit of the reaction temperature is preferably 120° C. or less, more preferably 105° C. or less, and still more preferably 95° C. or less. When the reaction temperature is not less than the lower limit value above, the introduction rate of a functional group can be increased, and when the reaction temperature is not more than the upper limit above, deterioration or volatilization of the solvent can be advantageously suppressed.

The pressure in the amination reaction is not particularly limited, and the reaction may be conducted in the range from around atmospheric pressure to slightly under pressure. Specifically, the pressure is, in terms of absolute pressure, preferably from 0.1 to 0.5 MPa, and more preferably from 0.1 to 0.3 MPa.

In the amination reaction, although the reaction time is not particularly limited as long as the reaction proceeds, the reaction time is usually from 0.5 to 15 hours, preferably from 2 to 12 hours. When the reaction time is in the range above, the reaction is allowed to sufficiently proceed with suppressing a side reaction of the aminated styrene crosslinked copolymer produced.

Unreacted iminodiacetonitrile in the amination reaction may be extracted from the solvent for an amination reaction after the completion of the amination reaction and recycled.

<Hydrolysis Reaction>

The aminated styrene crosslinked copolymer obtained by the above-described amination reaction is hydrolyzed, and the target iminodiacetic acid chelating resin can thereby be obtained.

In the production method of the present invention, the aminated styrene crosslinked copolymer obtained by an amination reaction has a nitrile group derived from iminodiacetonitrile, and this nitrile group is hydrolyzed with an acid, an alkali, etc. and can thereby be converted to an iminodiacetic acid group. In addition, the chelating resin is generally used in the loaded form and therefore, the copolymer is preferably hydrolyzed with an alkali, so that the resin after hydrolysis can be directly made into a product.

The acid used for the hydrolysis reaction is preferably a strong acid, and examples thereof include hydrochloric acid, sulfuric acid, and nitric acid, with sulfuric acid being preferred. One of these acids may be used alone, or two or more thereof may be used in combination.

As the alkali used for the hydrolysis reaction, sodium hydroxide, potassium hydroxide, calcium hydroxide, etc. are preferred, and among these, sodium hydroxide and potassium hydroxide are more preferred. Only one of these alkalis may be used, or two or more thereof may be used in combination.

The alkali is preferably used in the form of an aqueous solution, and the concentration thereof is preferably from 5 to 60% by weight, more preferably from 15 to 50% by weight.

The temperature in the hydrolysis reaction is preferably 40° C. or more, and more preferably 50° C. or more. The upper limit thereof is preferably 100° C. or less, and more preferably 90° C. or less.

The pressure in the hydrolysis reaction is not particularly limited, similarly to the amination reaction, and the reaction may be conducted in the range from around atmospheric pressure to slightly under pressure. Specifically, the pressure is, in terms of absolute pressure, preferably from 0.1 to 0.5 MPa, and more preferably from 0.1 to 0.3 MPa.

In the hydrolysis reaction, although the reaction time is not particularly limited as long as the reaction sufficiently proceeds, the reaction time is usually from 0.5 to 15 hours, and preferably from 2 to 12 hours.

The iminodiacetic acid chelating resin obtained by the hydrolysis reaction is washed with water, regenerated with an aqueous sodium hydroxide solution so as to adjust the volume ratio of Na form/H form to a desired value, and then made into a product. At the time of water washing after the hydrolysis reaction, when an alkali was used in the hydrolysis reaction, washing with an acid may also be performed. The volume ratio of Na form/H form of the obtained iminodiacetic acid chelating resin can be controlled by adjusting the sodium hydroxide concentration and amount of the aqueous sodium hydroxide solution at the time of regeneration after washing.

According to the production method of an iminodiacetic acid chelating resin of the present invention, an iminodiacetic acid group can be efficiently introduced, in comparison with the conventional production method using a catalytic reaction. Consequently, an iminodiacetic acid chelating resin obtained by the present invention exhibits good heavy metal absorptivity and, for example, as demonstrated in Examples later, copper (Cu) adsorptivity is very high.

[Iminodiacetic Acid Chelating Resin]

(1) A first embodiment of the iminodiacetic acid chelating resin of the present invention is as follows:

an iminodiacetic acid chelating resin wherein the infrared absorption spectrum obtained by infrared absorption analysis satisfies the following formula (1):

$$0.85\% \leq ((\text{transmittance at } 2{,}000 \text{ cm}^{-1}) - (\text{transmittance at } 2{,}200 \text{ cm}^{-1}))/(\text{transmittance at } 2{,}000 \text{ cm}^{-1}) \times 100 \leq 5\% \quad (1)$$

Here, each of "2,000 $cm^{-1}$", "2,200 $cm^{-1}$", and the later-described "2,100 $cm^{-1}$" and "2,300 $cm^{-1}$" indicates a wavelength (wavenumber) in the infrared absorption spectrum.

In the following, the value calculated by "((transmittance at 2,000 $cm^{-1}$)−(transmittance at 2,200 $cm^{-1}$))/(transmittance at 2,000 $cm^{-1}$)×100" in formula (1) is sometimes referred to as "T(1) value".

In the present invention, the infrared absorption analysis of the iminodiacetic acid chelating resin is performed by measuring the infrared absorption spectrum (hereinafter, sometimes referred to as "IR spectrum") according to the KBr method by means of "FT-IR Model 410" manufactured by JASCO Corporation. In this connection, at the time of measurement of an IR spectrum, the iminodiacetic acid chelating resin is in the Na form.

When the T(1) value of the iminodiacetic acid chelating resin is from 0.85 to 5%, the resin provides a high metal adsorption amount.

Here, for the reason that the adsorption amount of a metal such as Cu is more improved, the lower limit value of the T(1) value is preferably 0.95%, more preferably 1.0%, still more preferably 1.1%, and yet still more preferably 1.2%. The upper limit value of the T(1) value is preferably 4.5%, more preferably 4.0%, still more preferably 3.5%, and yet still more preferably 3.0%.

In the first embodiment of the iminodiacetic acid chelating resin of the present invention, the infrared absorption spectrum obtained by infrared absorption analysis preferably has a downwardly convex peak in the range of 2,100 to 2,300 cm$^{-1}$ (hereinafter, sometimes referred to as "specific peak").

In the present invention, the "infrared absorption spectrum obtained by infrared absorption analysis preferably has a downwardly convex peak in the range of 2,100 to 2,300 cm$^{-1}$" means to have a minimum value in the range of 2,100 to 2,300 cm$^{-1}$ of the infrared absorption spectrum.

The iminodiacetic acid chelating resin satisfying formula (1) and preferably having the specific peak can be obtained, for example, by controlling the amination reaction conditions or hydrolysis reaction conditions at the time of producing the iminodiacetic acid chelating resin by the above-described production method of an iminodiacetic acid chelating resin of the present invention. More specifically, in the IR spectrum, the specific peak indicates the presence of C—N stretching vibration derived from iminodiacetonitrile, and the T(1) value indicates that an appropriate amount of C—N group derived from iminodiacetonitrile is present within the iminodiacetic acid chelating resin. Accordingly, an iminodiacetic acid chelating resin exhibiting these properties can be obtained by performing an amination reaction under appropriate reaction conditions by use of iminodiacetonitrile and an appropriate amount of catalyst and performing a hydrolysis reaction under appropriate reaction conditions. The same holds for the later-described second embodiment of the iminodiacetic acid chelating resin of the present invention.

In the first embodiment of the iminodiacetic acid chelating resin of the present invention, from the viewpoint of increasing the adsorption amount of a metal such as Cu, the degree of porosity is preferably from 60 to 90%. In particular, the lower limit of the degree of porosity is more preferably 65%, still more preferably 70%, and yet still more preferably 75%. The upper limit value of the degree of porosity is more preferably 88%, still more preferably 85%, yet still more preferably 83%, and even yet still more preferably 80%.

The degree of porosity of the iminodiacetic acid chelating resin can be controlled, as described above, by adjusting the used amount of the porosifying agent at the time of production of a styrene crosslinked copolymer.

In the first embodiment of the iminodiacetic acid chelating resin of the present invention, from the viewpoint of increasing the adsorption amount of a metal such as Cu, the water amount in the resin is preferably from 50 to 75%. In particular, the lower limit of the water amount is more preferably 55%, still more preferably 60%, and yet still more preferably 65%. The upper limit value is more preferably 72%, still more preferably 70%, and yet still more preferably 68%.

The water amount in the iminodiacetic acid chelating resin is measured by the method described later in the section of Examples.

When the water amount is 50% or more, the resin exhibits good water permeability, and the adsorption amount of a metal such as Cu increases. However, if the water amount exceeds 75%, the amount of the exchange group relative to the volume of the resin is reduced and therefore, the adsorption amount per volume decreases.

An iminodiacetic acid chelating resin having a water amount of 50 to 75% may be produced, for example, by controlling the crosslinking degree and porosity degree of the iminodiacetic acid chelating resin to fall in appropriate ranges. The same holds for the later-described second embodiment of the iminodiacetic acid chelating resin of the present invention.

In the first embodiment of the iminodiacetic acid chelating resin of the present invention, from the viewpoint of increasing the adsorption amount of a metal such as Cu, the volume ratio of Na form/H form, i.e., the volume ratio between Na-form iminodiacetic acid chelating resin and H-form iminodiacetic acid chelating resin (hereinafter, sometimes referred to as "Na/H volume ratio"), is preferably from 1.2 to 1.8. In particular, the lower limit of the Na/H volume ratio is more preferably 1.3, still more preferably 1.4, yet still more preferably 1.42, and even yet still more preferably 1.45. The upper limit value is more preferably 1.7, and still more preferably 1.6.

The Na/H volume ratio is affected by the matrix structure (degree of crosslinking, porosity) of the resin or the amount of functional group introduced, and with the same matrix, as the amount of functional group introduced is larger, the volume ratio becomes higher. Because, even in the same resin, the water retention amount is larger in the Na-form iminodiacetic acid chelating resin due to action of Na in the functional group.

In this connection, the Na/H volume ratio of the iminodiacetic acid chelating resin is measured by the method described later in the section of Examples.

When the Na/H volume ratio is 1.2 or more, since the number of exchange groups utilized for adsorption is large and water is appropriately contained in the resin, the adsorption amount of a metal such as Cu increases. However, if the Na/H volume ratio exceeds 1.8, the swelling/shrinking ratio becomes excessively large, and it is highly likely that a pressure drop is generated at the time of passing liquid and the apparatus is broken.

An iminodiacetic acid chelating resin having an Na/H volume ratio in the range above may be produced, for example, by controlling the degree of crosslinking of the iminodiacetic acid chelating resin to fall in an appropriate range, or in the production of the iminodiacetic acid chelating resin, as described above, by adjusting the sodium hydroxide concentration and amount of the aqueous sodium hydroxide solution at the time of regeneration after washing.

In the first embodiment of the iminodiacetic acid chelating resin of the present invention, from the viewpoint of increasing the adsorption amount of a metal such as Cu, the degree of crosslinking is preferably from 4 to 7%. In particular, the lower limit of the degree of crosslinking is more preferably 4.5%, still more preferably 5%. The upper limit value is more preferably 6.5%, still more preferably 6.3%, and yet still more preferably 6%. A crosslinking degree of 4% or more is preferred, since the resin has sufficient strength, and a crosslinking degree of 7% or less is preferred, since the resin has sufficient adsorption performance.

The degree of crosslinking of the iminodiacetic acid chelating resin of the present invention can be controlled, as descried above, by adjusting the used amount of a raw material monomer in the production of a raw material styrene crosslinked copolymer. The same holds for the later-described second embodiment of the iminodiacetic acid chelating resin of the present invention.

(2) A second embodiment of the iminodiacetic acid chelating resin of the present invention is as follows:
an iminodiacetic acid chelating resin, wherein the water amount in the resin is from 50 to 75% and the volume ratio of Na form/H form is from 1.4 to 1.8.

The second embodiment of the iminodiacetic acid chelating resin of the present invention is characterized in that the water amount in the resin is from 50 to 75%. In particular, from the viewpoint of increasing the adsorption amount of a metal such as Cu, the lower limit of the water amount is preferably 55%, more preferably 60%, and still more preferably 65%. The upper limit value is preferably 72%, more preferably 70%, and still more preferably 68%.

The second embodiment of the iminodiacetic acid chelating resin of the present invention is characterized in that the volume ratio of Na form/H form is from 1.4 to 1.8. In particular, from the viewpoint of increasing the adsorption amount of a metal such as Cu, the lower limit of the Na/H volume ratio is preferably 1.42, and more preferably 1.45. The upper limit value is preferably 1.7, and more preferably 1.6.

As with the first embodiment of the present invention, also in the second embodiment of the present invention, the infrared absorption spectrum obtained by infrared absorption analysis preferably has a downwardly convex peak in the range of 2,100 to 2,300 cm$^{-1}$ (specific peak).

In addition, also in the second embodiment of the present invention, from the viewpoint of increasing the adsorption amount of a metal such as Cu, the degree of porosity is preferably from 60 to 90%. In particular, the lower limit of the degree of porosity is more preferably 65%, still more preferably 70%, and yet still more preferably 75%. The upper limit value is more preferably 88%, still more preferably 85%, yet still more preferably 83%, and even yet still more preferably 80%.

Furthermore, also in the second embodiment of the present invention, from the viewpoint of increasing the adsorption amount of a metal such as Cu, the degree of crosslinking is preferably from 4 to 7%. In particular, the lower limit of the degree of crosslinking is more preferably 4.5%, and still more preferably 5%. The upper limit value is more preferably 6.5%, still more preferably 6.3%, and yet still more preferably 6%.

EXAMPLES

Although the contents of the present invention are described more specifically below by referring to Examples, the present invention is not limited to the following Examples as long as its gist is observed. The values of various production conditions or evaluation results in the following Examples have a meaning as a preferable upper or lower limit in the embodiment of the present invention, and the preferable range may be a range defined by the combination of the above-described upper or lower limit value and the value in the following Examples or of the values in Examples.

[Evaluation Method]

The evaluation methods in Examples and Comparative Examples are described below.

(1) Degree of Crosslinking

Refer to DIAION MANUAL, issued by Mitsubishi Chemical Corporation, page 3.

(2) Degree of Porosity

The degree of porosity is calculated from the amount added of an organic solvent that is a porosifying agent, relative to raw material monomers at the time of production of a styrene-divinylbenzene crosslinked polymer, according to [(organic solvent (weight)/all monomers charged (weight))×100.

(3) Yield

The yield of the iminodiacetic acid chelating resin obtained by a series of reactions was determined by measuring the weight with an electron balance after the resin was drained at 3,000 rpm for 7 minutes by using a rotary centrifugal filter.

The yield is preferably larger and is suitably from 2.5 to 4.5 g/g-CMP (wet), preferably from 3.0 to 4.5 g/g-CMP (wet), more preferably from 3.5 to 4.5 g/g-CMP (wet), relative to the amount of the resin charged.

Here, [g/g-CMP (wet)] means the weight (g) per 1 g of the water-containing chloromethylated styrene crosslinked copolymer after draining by centrifugal filtration.

(4) Cu Adsorption Amount

After collecting 6 g of an iminodiacetic acid chelating resin (sample) deprived of attached water by centrifugal separation, accurately weighing and then putting in a 1 L stoppered Erlenmeyer flask were carried out, and 200 mL of an aqueous 0.05 M $CuCl_2$ solution was added thereto by means of a whole pipette. The Erlenmeyer flask was shaken for 6 hours in a constant-temperature shaker at (30±2)° C. After the completion of shaking, 5 mL of the supernatant was collected in a 300 mL conical beaker by means of a whole pipette.

After adding 90 mL of distilled water into the beaker, 1 mL of a buffer solution (Note 1 below) and a DOTITE PAN indicator (Note 2 below) were added, and the obtained mixture was titrated with 0.01 M-EDTA (titer: a (mL)).

As a blank test, an aqueous 0.05 M-$CuCl_2$ solution alone was titrated in the same manner as above (titer: b (mL)).

Using these results, the Cu adsorption amount was calculated according to the following formula.

A larger Cu adsorption amount is evaluated as indicating efficient introduction of an iminodiacetic acid and is preferable since it means that the Cu adsorption capacity is excellent.

$$[\text{Cu Adsorption amount (mmol/mL)}]=[\{(b-a) \times F \times 0.01 \times (200/5)\}]/[\text{sample (g)}/\{(\text{apparent density})/1000\}]$$

$$[\text{Cu Adsorption amount (mmol/g)}]=[\{(b-a) \times F \times 0.01 \times (200/5)\}]/[\text{sample (g)} \times \{100-(\text{water amount})/100\}]$$

(Note 1) Buffer solution: The total amount of a solution obtained by dissolving 5.8 mL of glacial acetic acid in 100 mL of water and the total amount of a solution obtained by dissolving 13.6 g of sodium acetate in 100 mL of water were mixed to prepare a buffer solution.

(Note 2) Indicator: 0.1 g of PAN: (1-(2'-pyridylazo)-2-naphthol) was used by dissolving it in 100 mL of methanol.

(Note 3) F: The titer of 0.01 M-EDTA.

(Note 4) Apparent density: About 150 g of an iminodiacetic acid chelating resin sample was collected; accurately weighed ($x_1$ (g)); and added to a measuring cylinder containing 500 mL of demineralized water, and the bottom was lightly tapped until a decrease in the volume was not observed, followed by reading the volume $x_2$ (mL), the apparent density was determined according to the following formula:

$$[\text{Apparent density (g/L)}]=\{(x_1(\text{g}))/(x_2(\text{mL}))\} \times 1000$$

(Note 5) Water amount: The water amount (%) of the iminodiacetic acid chelating resin sample determined in the following (5).

Here, as for the Cu adsorption amount (mmol/mL), the larger the numerical value, the better, since the adsorption amount per volume is large. In the present invention, an adsorption amount of 0.69 mmol/mL or more is particularly preferred.

In addition, as for the Cu adsorption amount (mmol/mL), the larger the numerical value, the better, because the adsorption amount per weight is large.

The Cu adsorption amount (mmol/g) corresponds to the amount of functional group introduced per dry resin weight and is an index indicating how much a functional group is chemically introduced. The Cu adsorption amount (mmol/mL) indicates the effective functional group amount per unit volume at the time of actual use in a column.

(5) Water Amount

An Na-form iminodiacetic acid chelating resin immersed in water was drained at 3,000 rpm for 7 minutes by using a rotary centrifugal filter. Thereafter, the water amount was calculated by the following procedure.

About 5 g of an iminodiacetic acid chelating resin sample was collected in a weighing bottle; accurately weighed ($W_1$ (g)); put in a vacuum dryer at 50±2° C., dried for 8 hours; allowed to cool in a desiccator; and measured for the dry weight ($W_2$ (g)) in the same manner, and the water amount (%) was calculated according to the following formula:

[Water content (%)]=[$W_1$(g)-$W_2$(g)]/[$W_1$(g)]×100

(6) Infrared Absorption Spectrum

The infrared absorption spectrum was measured by using the Na-form iminodiacetic acid chelating resin after the measurement of water content.

The infrared absorption spectrum was measured according to the KBr method by means of "FT-IR Model 410" manufactured by JASCO Corporation.

The transmittance at 2,000 $cm^{-1}$ and the transmittance at 2,200 $cm^{-1}$ were read from the infrared absorption spectrum obtained by infrared absorption analysis, and the T(1) value was calculated. In addition, the presence (A) or absence (C) of a downwardly convex peak (specific peak) in the range of 2,100 to 2,300 $cm^{-1}$ was confirmed.

(7) Na/H Volume Ratio

About 15 mL of an iminodiacetic acid chelating resin sample was put in a 25 mL measuring cylinder previously containing a small amount of demineralized water and after lightly tapping the bottom until a decrease in the volume was not observed, the volume $V_1$ (mL) of the sample portion was measured. The sample was transferred to a 300 mL beaker by using a small amount of demineralized water, and 200 mL of hydrochloric acid at a concentration of 1 mol/L was added; lightly mixed; and then left standing for 5 hours. Thereafter, the sample (resin) was repeatedly washed with demineralized water until the washing liquid became neutral. The sample after washing was, similarly to the above, transferred to a 25 mL measuring cylinder containing a small amount of demineralized water; the bottom was lightly tapped until a decrease in the volume was not observed; the volume $V_2$ (mL) of the sample portion was measured; and the volume ratio between the Na-form resin and the H-form resin was calculated.

[Na/H Volume ratio]=[$V_1$(mL)/$V_2$ (mL)]

(8) Iodine Concentration in Supernatant

A supernatant after adding 70 g of pure water to 7 g (wet) of iminodiacetic acid chelating resin and shaking it at 30° C. for 8 hours was analyzed by ICP-MS by adding hydrogen peroxide to make a constant volume.

The "g (wet)" as used herein means the weight of a drained iminodiacetic acid chelating resin after the resin was, as described later, drained at 3,000 rpm for 7 minutes by using a rotary centrifugal filter.

Example 1

<Chloromethylation Reaction>

In a 3 L four-neck flask equipped with a stirring blade, 900 g of chloromethyl methyl ether was added to 150 g of styrene-vinylbenzene copolymer, and the copolymer was swollen at room temperature (25° C.) for 30 minutes. Thereafter, 105 g of zinc(II) chloride was added; the temperature was raised to 50° C. over 2 hours; and the reaction was allowed to proceed for 9 hours. After the completion of reaction, cooling to 40° C. or less is carried out, and the catalyst was deactivated by adding 384 g of 35% by weight hydrochloric acid to obtain a chloromethylated styrene crosslinked copolymer.

<Distillation of Chloromethyl Methyl Ether>

After the chloromethylation reaction above, a distilling head and a distillation adaptor were attached to the four-neck flask, the bath temperature was raised to 113° C. over 4 hours and 40 minutes, and chloromethyl methyl ether was distilled off by holding the system at this temperature for 2.5 hours. At the time of temperature rise, 561 g of 35% by weight hydrochloric acid was added at an inner temperature of 46° C. over 2 hours.

After the reaction, the obtained reaction product was washed with water until it became neutral and then drained at 3,700 rpm for 10 minutes by using a rotary centrifugal filter.

<Amination Reaction>

In a 200 mL four-neck flask equipped with a stirring blade, 10.0 g (dry weight: 7.0 g) of the chloromethylated styrene crosslinked copolymer in a hydrous state obtained above was subjected to batch solvent displacement (50 mL×3 times) with isopropanol (IPA). Thereafter, 35 mL (about 45 g, 643 parts by weight per 100 parts by weight of the dry resin) of IPA was added, and 7.5 g (107 parts by weight per 100 parts by weight of the dry resin) of iminodiacetonitrile (IDN), 1.0 g (14 parts by weight per 100 parts by weight of the dry resin) of potassium iodide, and 3.6 g (51 parts by weight per 100 parts by weight of the dry resin) of sodium carbonate were further added and reacted at 90° C. for 8 hours to obtain an aminated styrene crosslinked copolymer.

The obtained reaction solution containing the copolymer was washed with water to remove remaining raw materials.

The conditions of these reactions are shown in Table 1.

<Hydrolysis Reaction>

Subsequently, 50 mL of an aqueous 30% by weight sodium hydroxide solution was added to the aminated styrene crosslinked copolymer (total amount) obtained above, and a hydrolysis reaction was performed at 80° C. for 6 hours. After the completion of reaction, water washing and washing with 100 mL of 2 N-hydrochloric acid were performed, and regeneration of the resin was then performed by using 100 mL of an aqueous 2 N-sodium hydroxide solution to obtain an iminodiacetic acid chelating resin.

The obtained resin was again washed with water and drained at 3,000 rpm for 7 minutes by using a rotary centrifugal filter. The yield (weight after draining) of the iminodiacetic acid chelating resin was 40.5 g.

<Evaluation>

The obtained iminodiacetic acid chelating resin was evaluated by the methods described above. The results are shown together in Table 1.

Examples 2 to 7 and Comparative Examples 1 to 7

Iminodiacetic acid chelating resins were obtained by performing amination and hydrolysis reactions in the same manner as in Example 1 except that a styrene-divinylbenzene copolymer having the crosslinking degree and porosity degree shown in Tables 1 and 2 was used and the amination reaction conditions and hydrolysis reaction conditions were changed as shown in Tables 1 and 2, and the obtained iminodiacetic acid chelating resins were evaluated by the methods described above. The results are shown together in Tables 1 and 2.

Figure 1:
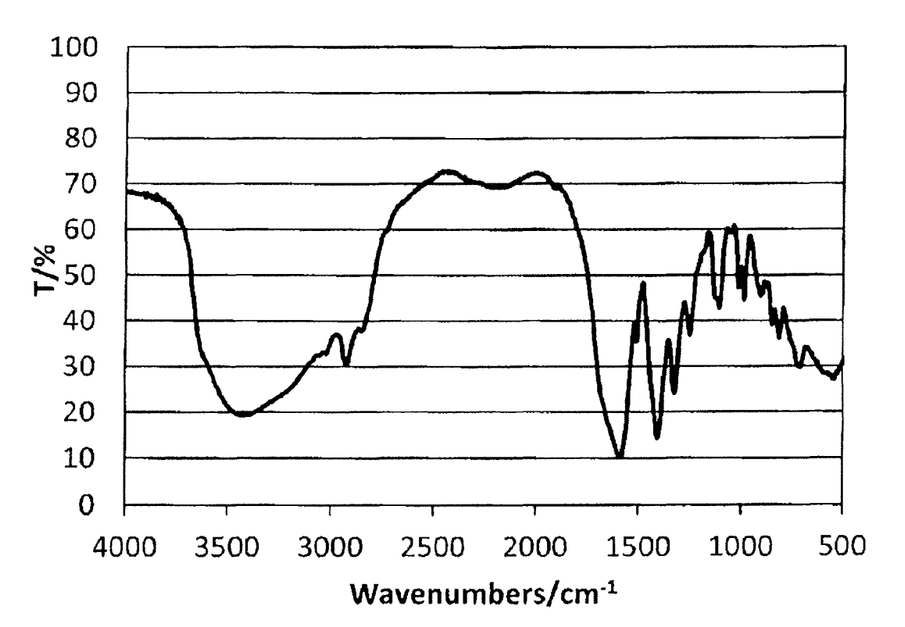
FIG. 1 is an IR spectrum chart of the iminodiacetic acid chelating resin of Example 5.

FIG. 1 illustrates an IR spectrum chart of the iminodiacetic acid chelating resin of Example 5. In FIG. 1, the presence of a downwardly convex peak can be read at approximately around 2,220 $cm^{-1}$.

In this connection, in Comparative Example 5 of Hydrolysis Reaction Condition (20% HCl), the hydrolysis reaction was performed in the same manner as in Example 1 except that an aqueous 20% by weight hydrochloric acid solution was used in place of an aqueous 30% by weight sodium hydroxide solution.

Explanatory notes about numerical values in Tables 1 and 2 are given below.

*1. In the Tables, the parenthesized numerical value in the column of chloromethylated styrene crosslinked copolymer means the weight on dry resin basis.

*2. In the Tables, [g/g-CMP (wet)] means the weight (g) per 1 g of the water-containing chloromethylated styrene crosslinked copolymer after draining by centrifugal filtration.

*3. In the Tables, [mL/g-CMP (wet)] means the volume (mL) per 1 g of the water-containing chloromethylated styrene crosslinked copolymer after draining by centrifugal filtration.

*4. In the Tables, the parenthesized numerical value in the column of aminating agent means the parts by weight of the aminating agent per 100 parts by weight (on dry resin basis) of the chloromethylated styrene crosslinked copolymer.

*5. In the Tables, the parenthesized numerical value in the column of catalyst means the parts by weight of the catalyst per 100 parts by weight (on dry resin basis) of the chloromethylated styrene crosslinked copolymer.

*6. In the Tables, "-" means that the aminating agent, catalyst or solvent was not used or the evaluation was not performed.

*7. In the Tables, the parenthesized numerical value in the column of yield means the weight (g) per 1 g of the water-containing chloromethylated styrene crosslinked copolymer after draining by centrifugal filtration.

TABLE 1

| | | | Example 1 | Example 2 | Example 3 | Example 4 | Example 5 | Example 6 |
|---|---|---|---|---|---|---|---|---|
| | Degree of crosslinking | [%] | 5 | 5.5 | 5.5 | 6 | 6 | 6 |
| | Degree of porosity | [%] | 80 | 75 | 80 | 70 | 75 | 80 |
| Amination reaction | Chloromethylated styrene crosslinked copolymer | [g] | 10 (7.0) | 10 (7.0) | 10 (7.0) | 10 (7.0) | 10 (7.0) | 10 (7.0) |
| | Aminating agent Iminodiacetonitrile | [g/g-CMP (wet)] | 0.75 (107.1) | 0.75 (107.1) | 0.75 (107.1) | 0.75 (107.1) | 0.75 (107.1) | 0.75 (107.1) |
| | Iminodiacetic acid ester | [g/g-CMP (wet)] | — | — | — | — | — | — |
| | Catalyst Potassium iodide | [g/g-CMP (wet)] | 0.1 (14.3) | 0.1 (14.3) | 0.1 (14.3) | 0.1 (14.3) | 0.1 (14.3) | 0.1 (14.3) |
| | Sodium iodide | [g/g-CMP (wet)] | — | — | — | — | — | — |
| | Dimethylaniline | [g/g-CMP (wet)] | — | — | — | — | — | — |
| | Solvent Isopropyl alcohol | [mL/g-CMP (wet)] | 3.5 | 3.5 | 3.5 | 3.5 | 3.5 | 3.5 |
| | Ethanol | [mL/g-CMP (wet)] | — | — | — | — | — | — |
| | Toluene | [mL/g-CMP (wet)] | — | — | — | — | — | — |
| | pH Adjusting agent Sodium carbonate | [g/g-CMP (wet)] | 0.36 | 0.36 | 0.36 | 0.36 | 0.36 | 0.36 |
| | Reaction time | [hours] | 8 | 8 | 8 | 8 | 8 | 8 |
| | Reaction temperature | [° C.] | 90 | 90 | 90 | 90 | 90 | 90 |
| Hydrolysis reaction | Conditions (30% NaOH or 20% HCl) | | 30% NaOH | 30% NaOH | 30% NaOH | 30% NaOH | 30% NaOH | 30% NaOH |
| | Reaction time | [hours] | 6 | 6 | 6 | 6 | 6 | 6 |
| | Reaction temperature | [° C.] | 80 | 80 | 80 | 80 | 80 | 80 |
| | Yield | [g] | 40.5 (4.05) | 35.6 (3.56) | 34.7 (3.47) | 36.1 (3.61) | 32.1 (3.21) | 31.6 (3.16) |
| Evaluation | Cu Adsorption capacity | [mmol/mL] | 0.66 | 0.70 | 0.66 | 0.82 | 0.68 | 0.64 |
| | | [mmol/g] | 3.01 | 2.96 | 3.01 | 2.74 | 2.90 | 2.89 |
| | Presence or absence of specific peak | | A | A | A | A | A | A |
| | T(1) Value | | 0.98 | 1.34 | 3.81 | 3.35 | 4.15 | 1.68 |
| | Water content | [%] | 68.71 | 67.30 | 68.42 | 59.76 | 66.73 | 68.49 |
| | Na/H Volume ratio | [—] | 1.53 | 1.54 | 1.46 | 1.46 | 1.45 | 1.45 |

| | | | Comparative Example 1 | Comparative Example 2 | Comparative Example 3 | Comparative Example 4 | Comparative Example 5 |
|---|---|---|---|---|---|---|---|
| | Degree of crosslinking | [%] | 6 | 6.5 | 8 | 7 | 7 |
| | Degree of porosity | [%] | 75 | 75 | 75 | 75 | 75 |
| Amination reaction | Chloromethylated styrene crosslinked copolymer | [g] | 357 (250) | 10 (7.0) | 10 (7.0) | 10 (7.0) | 10 (7.0) |
| | Aminating agent Iminodiacetonitrile | [g/g-CMP (wet)] | — | 0.75 (107.1) | 0.75 (107.1) | 0.75 (107.1) | 0.75 (107.1) |
| | Iminodiacetic acid ester | [g/g-CMP (wet)] | 0.63 (89.8) | — | — | — | — |
| | Catalyst Potassium iodide | [g/g-CMP (wet)] | 0.06 (8.6) | 0.1 (14.3) | 0.1 (14.3) | — | 0.1 (14.3) |
| | Sodium iodide | [g/g-CMP (wet)] | — | — | — | — | — |
| | Dimethylaniline | [g/g-CMP (wet)] | — | — | — | — | — |

TABLE 1-continued

|  |  |  |  |  |  |  |  |  |
|---|---|---|---|---|---|---|---|---|
|  | Solvent | Isopropyl alcohol | [mL/g-CMP (wet)] | — | 3.5 | 3.5 | 3.5 | 3.5 |
|  |  | Ethanol | [mL/g-CMP (wet)] | 2.1 | — | — | — | — |
|  |  | Toluene | [mL/g-CMP (wet)] | — | — | — | — | — |
|  | pH Adjusting agent | Sodium carbonate | [g/g-CMP (wet)] | 0.23 | 0.36 | 0.36 | 0.36 | 0.36 |
|  |  | Reaction time | [hours] | 8 | 8 | 8 | 8 | 8 |
|  |  | Reaction temperature | [° C.] | 75 | 90 | 90 | 80 | 80 |
| Hydrolysis reaction | Conditions (30% NaOH or 20% HCl) |  |  | 30% NaOH | 30% NaOH | 30% NaOH | 30% NaOH | 20% HCl |
|  | Reaction time |  | [hours] | 6 | 6 | 6 | 6 | 6 |
|  | Reaction temperature |  | [° C.] | 60 | 80 | 80 | 80 | 80 |
|  | Yield |  | [g] | 27.5 (0.077) | 27.4 (2.74) | 20.9 (2.09) | 10.47 (1.047) | 13.18 (1.318) |
| Evaluation | Cu Adsorption capacity |  | [mmol/mL] | 0.66 | 0.68 | 0.59 | 0.04 | 0.02 |
|  |  |  | [mmol/g] | 2.68 | 2.62 | 2.11 | 0.13 | 0.07 |
|  | Presence or absence of specific peak |  |  | C | A | A | — | — |
|  | T(1) Value |  |  | 0.83 | 7.48 | 5.54 | — | — |
|  | Water content |  | [%] | 65.7 | 63.10 | 59.60 | 46.1 | 46.8 |
|  | Na/H Volume ratio |  | [—] | 1.23 | 1.36 | 1.18 | 0.97 | 1.22 |

[Evaluation of Results]

The following various matters are seen from Table 1.

The iminodiacetic acid chelating resins of Examples 1 to 6 using iminodiacetonitrile as the aminating agent and isopropyl alcohol as the solvent satisfy the formula (1) and have excellent adsorption performance, showing a water amount of 50 to 75%; a volume ratio of Na form/H form of 1.4 to 1.8; and larger Cu adsorption amounts per unit volume and unit weight of the resin than in Comparative Example 1 wherein iminodiacetic acid ester is used as the aminating agent and ethanol is used as the solvent and Comparative Example 4 wherein an amination reaction catalyst is not used.

The iminodiacetic acid chelating resins of Examples 1 to 6 using a styrene-divinylbenzene copolymer having a degree of crosslinking of 5 to 6% satisfy the formula (1) and have a water amount of 50 to 75% and a volume ratio of Na form/H form of 1.4 to 1.8. On the other hand, in Comparative Examples 2 and 3 using a styrene-divinylbenzene copolymer having a degree of crosslinking of 6.5% or 8.0%, the T(1) value exceeds 5%, failing in satisfying formula (1), and the volume ratio of Na form/H form is less than 1.4. Accordingly, in Examples 1 to 6, the Cu adsorption amounts per unit volume and unit weight of the chelating resin are larger than in Comparative Examples 2 and 3, and the adsorption performance is excellent.

The iminodiacetic acid chelating resins of Examples 1 to 6 using NaOH for the hydrolysis reaction satisfy the formula (1) and have excellent adsorption performance, showing larger Cu adsorption amounts per unit volume and unit weight of the chelating resin than in Comparative Example 5 using HCl for the hydrolysis reaction.

Furthermore, in Examples 1 to 6, the yield of the iminodiacetic acid chelating resin is large in comparison with Comparative Examples 1 to 5, and this fact also reveals that the amount of an iminodiacetic acid group introduced is large.

Having large Cu adsorption amounts per unit volume and unit weight of the chelating resin means that the introduction ratio of an iminodiacetic acid group as an adsorbing group in the resin is large.

In addition, having a large water amount in the resin means that the water permeability as a chelating resin is high, and indicates that the adsorption capacity per hour is excellent; and having a high Na/H volume ratio means that the number of substituents contributing to ion adsorption is large, and therefore indicates that the adsorption efficiency per unit resin amount is high.

In this connection, in Comparative Examples 2 and 3 where the degree of crosslinking is relatively high, it is presumed that an iminodiacetic acid group as an adsorbing group is less likely to be introduced into the resin, resulting in a low volume ratio of Na form/H form, and since hydrolysis is difficult, the T(1) value exceeds 5%. In Comparative Example 4 where an amination reaction catalyst is not used, the introduction ratio of an iminodiacetic acid group as an adsorbing group in the resin was extremely reduced, and the volume ratio of Na form/H form showed a low value. In Comparative Example 5 where HCl is used for the hydrolysis reaction, the hydrolysis did not proceed sufficiently, and the amount of an iminodiacetic acid group as an adsorbing group in the resin was therefore decreased. As a result, the volume ratio of Na form/H form showed a low value.

TABLE 2

|  |  |  |  | Example 2 | Example 5 | Example 7 | Comparative Example 4 |
|---|---|---|---|---|---|---|---|
| Amination reaction | Degree of crosslinking |  | [%] | 5.5 | 6 | 6 | 7 |
|  | Degree of porosity |  | [%] | 75 | 75 | 75 | 75 |
|  | Chloromethylated styrene crosslinked copolymer |  | [g] | 10 (7.0) | 10 (7.0) | 10 (7.0) | 10 (7.0) |
|  | Aminating agent | Iminodiacetonitrile | [g/g-CMP (wet)] | 0.75 (107.1) | 0.75 (107.1) | 0.75 (107.1) | 0.75 (107.1) |
|  |  | Iminodiacetic acid ester | [g/g-CMP (wet)] | — | — | — | — |
|  | Catalyst | Potassium iodide | [g/g-CMP (wet)] | 0.1 (14.3) | 0.1 (14.3) | — | — |
|  |  | Sodium iodide | [g/g-CMP (wet)] | — | — | 0.09 (12.9) | — |

TABLE 2-continued

|  |  |  |  |  |  |  |  |
|---|---|---|---|---|---|---|---|
|  | Solvent | Dimethylaniline | [g/g-CMP (wet)] | — | — | — | — |
|  |  | Isopropyl alcohol | [mL/g-CMP (wet)] | 3.5 | 3.5 | 3.5 | 3.5 |
|  |  | Ethanol | [mL/g-CMP (wet)] | — | — | — | — |
|  |  | Toluene | [mL/g-CMP (wet)] | — | — | — | — |
|  | pH Adjusting agent | Sodium carbonate | [g/g-CMP (wet)] | 0.36 | 0.36 | 0.36 | 0.36 |
|  |  | Reaction time | [hours] | 8 | 8 | 8 | 8 |
|  |  | Reaction temperature | [° C.] | 90 | 90 | 90 | 80 |
| Hydrolysis reaction |  | Condition (30% NaOH or 20% HCl) |  | 30% NaOH | 30% NaOH | 30% NaOH | 30% NaOH |
|  |  | Reaction time | [hours] | 6 | 6 | 6 | 6 |
|  |  | Reaction temperature | [° C.] | 80 | 80 | 80 | 80 |
|  |  | Yield | [g] | 35.6 (3.56) | 32.1 (3.21) | 31.6 (3.16) | 10.47 (1.047) |
| Evaluation |  | Cu Adsorption capacity | [mmol/mL] | 0.70 | 0.68 | 0.74 | 0.04 |
|  |  |  | [mmol/g] | 2.96 | 2.90 | 2.82 | 0.13 |
|  |  | Iodine concentration in supernatant | [ng/g] | 500 | — | 660 | 0.7 |
|  |  | Water content | [%] | 67.30 | 66.73 | 64.2 | 46.1 |
|  |  | Na/H volume ratio | [—] | 1.54 | 1.45 | 1.47 | 0.97 |

|  |  |  |  | Comparative Example 6 | Comparative Example 7 | Reference Comparative Example (Comparative Example 5) |
|---|---|---|---|---|---|---|
|  | Degree of crosslinking | [%] |  | 6 | 6 | 7 |
|  | Degree of porosity | [%] |  | 75 | 75 | 75 |
| Amination reaction | Chloromethylated styrene crosslinked copolymer | [g] |  | 10 (7.0) | 10 (7.0) | 10 (7.0) |
|  | Aminating agent | Iminodiacetonitrile | [g/g-CMP (wet)] | 1.0 (142.9) | 1.0 (142.9) | 0.75 (107.1) |
|  |  | Iminodiacetic acid ester | [g/g-CMP (wet)] | — | — | — |
|  | Catalyst | Potassium iodide | [g/g-CMP (wet)] | — | — | 0.1 (14.3) |
|  |  | Sodium iodide | [g/g-CMP (wet)] | — | — | — |
|  |  | Dimethylaniline | [g/g-CMP (wet)] | 1.25 (178.6) | 1.25 (178.6) | — |
|  | Solvent | Isopropyl alcohol | [mL/g-CMP (wet)] | — | 3.5 | 3.5 |
|  |  | Ethanol | [mL/g-CMP (wet)] | — | — | — |
|  |  | Toluene | [mL/g-CMP (wet)] | 3.5 | — | — |
|  | pH Adjusting agent | Sodium carbonate | [g/g-CMP (wet)] | 0.36 | 0.36 | 0.36 |
|  |  | Reaction time | [hours] | 8 | 8 | 8 |
|  |  | Reaction temperature | [° C.] | 80 | 75 | 80 |
| Hydrolysis reaction |  | Condition (30% NaOH or 20% HCl) |  | 30% NaOH | 30% NaOH | 20% HCl |
|  |  | Reaction time | [hours] | 6 | 6 | 6 |
|  |  | Reaction temperature | [° C.] | 80 | 80 | 80 |
|  |  | Yield | [g] | 25.9 (2.59) | 18.7 (1.87) | 13.18 (1.318) |
| Evaluation |  | Cu Adsorption capacity | [mmol/mL] | 0.59 | 0.44 | 0.02 |
|  |  |  | [mmol/g] | 2.26 | 1.45 | 0.07 |
|  |  | Iodine concentration in supernatant | [ng/g] | — | — | 590 |
|  |  | Water content | [%] | — | — | 46.8 |
|  |  | Na/H volume ratio | [—] | — | — | 1.22 |

[Evaluation of Results]

The following various matters are seen from Table 2.

The iminodiacetic acid chelating resins of Examples 2, 5 and 7 using potassium iodide or sodium iodide as the amination reaction catalyst satisfy the formula (1) and have a water amount of 50 to 75% and a volume ratio of Na form/H form of 1.4 to 1.8. On the other hand, in Comparative Example 4 wherein an amination reaction catalyst was not used, the volume ratio of Na form/H form is less than 1.4. Furthermore, in Examples 2, 5 and 7, the Cu adsorption amounts per unit volume and unit weight of the chelating resin are larger than in Comparative Example 4 and Comparative Examples 6 and 7 using dimethylaniline as the amination reaction catalyst, and the adsorption performance is excellent.

In this connection, in all of resins produced by the same method as in Examples 2 and 7 using potassium iodide or sodium iodide as the amination reaction catalyst and the iminodiacetic acid chelating resin of Reference Comparative Example (Comparative Example 5), the iodine concentration in the supernatant was 500 ng/g or more. On the other hand, in the iminodiacetic acid chelating resin of Comparative Example 4 wherein an amination reaction catalyst is not used, the iodine concentration in the supernatant showed an extremely low value.

While the present invention has been described in detail and with reference to specific embodiments thereof, it will be apparent to one skilled in the art that various changes and modifications can be made therein without departing from the spirit and scope of the present invention. This application is based on Japanese Patent Application (Patent Application No. 2015-124787) filed on Jun. 22, 2015, and the contents of which are incorporated herein by way of reference.

INDUSTRIAL APPLICABILITY

According to the present invention, an iminodiacetic acid chelating resin with excellent separation capacity is provided. In addition, a method for producing an iminodiacetic acid chelating resin, where an iminodiacetic acid group can be effectively introduced into a chloromethylated styrene crosslinked copolymer under mild conditions, is provided.

The iminodiacetic acid chelating resin provided by the present invention has high metal adsorptivity and is therefore useful over a wide range of fields such as heavy metal removal from salt and purification of chemicals.

The invention claimed is:

1. An iminodiacetic acid chelating resin, wherein a water amount in the resin is from 50 to 75% and a volume ratio of Na form/H form is from 1.4 to 1.8, and
wherein infrared absorption spectrum obtained by infrared absorption analysis has a downwardly convex peak in the range of 2,100 to 2,300 cm$^{-1}$.

2. The iminodiacetic acid chelating resin according to claim 1, wherein a degree of porosity of the iminodiacetic acid chelating resin is from 60 to 90%.

3. The iminodiacetic acid chelating resin according to claim 1, wherein a degree of crosslinking of the iminodiacetic acid chelating resin is from 4 to 7%.

4. A method for producing the iminodiacetic acid chelating resin of claim 1, the method comprising:
aminating a chloromethylated styrene crosslinked copolymer with iminodiacetonitrile, to obtain an aminated styrene crosslinked copolymer; and
hydrolyzing the aminated styrene crosslinked copolymer, wherein an alcohol is used as a solvent for aminating the chloromethylated styrene crosslinked copolymer.

5. The method according to claim 4, wherein sodium iodide and/or potassium iodide is used as a catalyst for aminating the chloromethylated styrene crosslinked copolymer.

6. A method for producing the iminodiacetic acid chelating resin according to claim 1, the method comprising:
aminating a chloromethylated styrene crosslinked copolymer with iminodiacetonitrile, to obtain an aminated styrene crosslinked copolymer; and
hydrolyzing the aminated styrene crosslinked copolymer,
wherein sodium iodide and/or potassium iodide is used as a catalyst for aminating the chloromethylated styrene crosslinked copolymer.

7. The method according to claim 5, wherein the catalyst is used in an amount from 0.1 to 30 parts by weight per 100 parts by weight (on dry resin basis) of the chloromethylated styrene crosslinked copolymer.

8. The method according to claim 4, wherein the iminodiacetonitrile is used in an amount from 40 to 200 parts by weight per 100 parts by weight (on dry resin basis) of the chloromethylated styrene crosslinked copolymer.

9. The method according to claim 4, wherein a reaction temperature for aminating the chloromethylated styrene crosslinked copolymer is from 40 to 120° C. and a reaction time for aminating the chloromethylated styrene crosslinked copolymer is from 0.5 to 15 hours.

10. The method according to claim 4, wherein a boiling point of the solvent for aminating the chloromethylated styrene crosslinked copolymer is from 30 to 180° C. and the solvent is used in an amount from 100 to 3,000 parts by weight per 100 parts by weight (on dry resin basis) of the chloromethylated styrene crosslinked copolymer.

11. The method according to claim 4, wherein an aliphatic alcohol containing branched chain and having a carbon number of 3 to 4 is used as the solvent for aminating the chloromethylated styrene crosslinked copolymer.

12. The method according to claim 4, wherein the hydrolyzing of the aminated styrene crosslinked copolymer is performed in the presence of at least one aqueous alkali solution selected from the group consisting of an aqueous sodium hydroxide solution, an aqueous potassium hydroxide solution, and an aqueous calcium hydroxide solution, or at least one strong acid selected from the group consisting of sulfuric acid, hydrochloric acid, and nitric acid.

13. The iminodiacetic acid chelating resin according to claim 1, wherein a degree of crosslinking of the iminodiacetic acid chelating resin is from 4 to 6%.

* * * * *